(12) United States Patent
Curti et al.

(10) Patent No.: US 8,740,808 B2
(45) Date of Patent: Jun. 3, 2014

(54) ADAPTIVE TEMPERATURE SENSOR FOR BREATH MONITORING DEVICE

(75) Inventors: James N. Curti, Bakersfield, CA (US); Kyle L. Adriance, Bakersfield, CA (US); Eric C. Land, Bakersfield, CA (US)

(73) Assignee: Salter Labs, Arvin, CA (US)

( * ) Notice: Subject to any disclaimer, the term of this patent is extended or adjusted under 35 U.S.C. 154(b) by 657 days.

(21) Appl. No.: 12/996,511

(22) PCT Filed: Jun. 5, 2009

(86) PCT No.: PCT/US2009/046388
§ 371 (c)(1),
(2), (4) Date: Apr. 12, 2011

(87) PCT Pub. No.: WO2009/149336
PCT Pub. Date: Dec. 10, 2009

(65) Prior Publication Data
US 2011/0301484 A1    Dec. 8, 2011

Related U.S. Application Data

(63) Continuation-in-part of application No. 12/348,599, filed on Jan. 5, 2009, now abandoned, which is a continuation-in-part of application No. 12/134,787, filed on Jun. 6, 2008, now abandoned.

(60) Provisional application No. 61/174,704, filed on May 1, 2009.

(51) Int. Cl.
*A61B 5/08* (2006.01)

(52) U.S. Cl.
USPC .......................................... 600/538; 600/537

(58) Field of Classification Search
USPC ........................................ 600/529–543, 549
See application file for complete search history.

(56) References Cited

U.S. PATENT DOCUMENTS

| 2,021,491 | A |   | 11/1935 | Ruben |
|---|---|---|---|---|
| 4,106,505 | A |   | 8/1978 | Salter et al. |
| 4,777,963 | A | * | 10/1988 | McKenna ...................... 600/537 |
| 4,808,160 | A |   | 2/1989 | Timmons et al. |
| 5,069,222 | A | * | 12/1991 | McDonald, Jr. .............. 600/537 |
| 5,190,048 | A | * | 3/1993 | Wilkinson ..................... 600/537 |

(Continued)

FOREIGN PATENT DOCUMENTS

WO      WO 97/18752    *   5/1997   ............... A61B 5/08

OTHER PUBLICATIONS

Brian M. McGinley et al. A Nasal Cannula Can Be Used to Treat Obstructive Sleep Apnea, American Journal of Respiratory and Critical Care Medicine, Mar. 15, 2007, pp. 194-200, vol. 176.

(Continued)

*Primary Examiner* — Patricia Mallari
*Assistant Examiner* — Tiffany Weston
(74) *Attorney, Agent, or Firm* — Davis & Bujold, PLLC; Michael J. Bujold

(57) ABSTRACT

A system and method for sleep monitoring, diagnosing and sensing temperature and pressure for a breathing cycle of a patient including a sensing device suitable for both nasal and oral breath monitoring for measuring respiratory air wave and airflow information during a sleep apnea diagnostic session and processing the acquired air wave and airflow breathing information for input to conventional polysomnography equipment.

12 Claims, 13 Drawing Sheets

(56) References Cited

U.S. PATENT DOCUMENTS

| | | | |
|---|---|---|---|
| 5,311,875 A * | 5/1994 | Stasz | 600/537 |
| 5,682,881 A | 11/1997 | Winthrop et al. | |
| 5,752,511 A | 5/1998 | Simmons et al. | |
| 6,165,133 A | 12/2000 | Rapoport et al. | |
| 6,342,040 B1 | 1/2002 | Starr et al. | |
| 6,786,475 B2 | 9/2004 | Salter et al. | |
| 7,080,645 B2 | 7/2006 | Genger et al. | |
| 7,087,027 B2 | 8/2006 | Page | |
| 7,137,389 B2 | 11/2006 | Berthon-Jones | |
| 7,152,604 B2 | 12/2006 | Hickle et al. | |
| 7,297,119 B2 | 11/2007 | Westbrook et al. | |
| 2002/0185131 A1 | 12/2002 | Madaus et al. | |
| 2004/0112382 A1 | 6/2004 | Schneider et al. | |
| 2006/0037614 A1 | 2/2006 | Madaus et al. | |
| 2006/0060198 A1 | 3/2006 | Aylsworth et al. | |
| 2006/0272641 A1 | 12/2006 | Madaus et al. | |
| 2006/0283446 A1 * | 12/2006 | Chua et al. | 128/200.26 |
| 2007/0093724 A1 * | 4/2007 | Nakano | 600/538 |
| 2008/0051674 A1 | 2/2008 | Davenport et al. | |

OTHER PUBLICATIONS

Dr. David Rapoport, M.D., Robert Norman, M.S., R.R.T., Michael Nielson, R.R.T., R.PSG.T., Nasal Pressure Airflow Measurement, Pro-Tech Services, Inc., Copyright 2001.

* cited by examiner

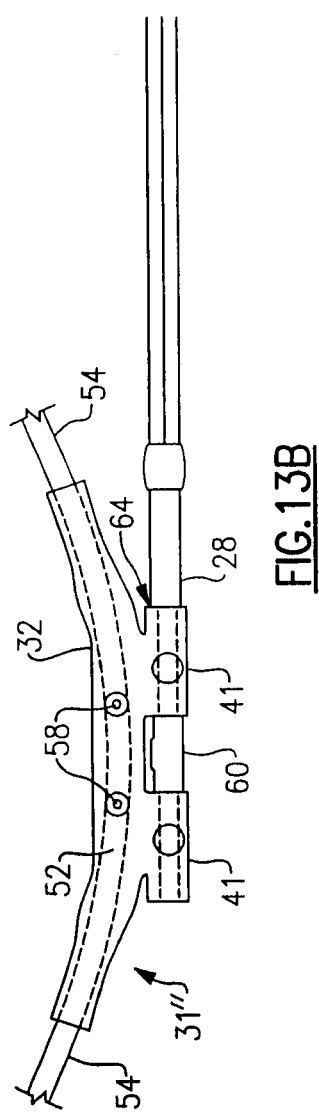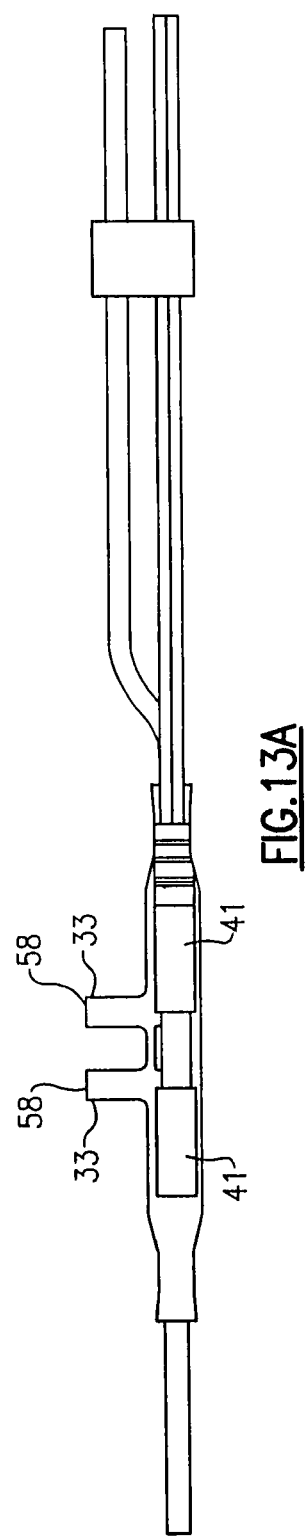

ADAPTIVE TEMPERATURE SENSOR FOR BREATH MONITORING DEVICE

FIELD OF THE INVENTION

The present invention relates to a sleep monitoring and diagnosing system including a temperature sensing and pressure sensing device suitable for both nasal and oral breath monitoring for measuring respiratory air wave and airflow information during a sleep apnea diagnostic session and processing the acquired air wave and airflow breathing information for input to conventional polysomnography equipment. The temperature and pressure sensing devices can be used individually or concurrently and, when utilized together, have a structural and signal based relationship which facilitates obtaining a verified output representative of the patient's breathing patterns.

BACKGROUND OF THE INVENTION

Sleep apnea (SA) is a common disorder observed in the practice of sleep medicine and is responsible for more mortality and morbidity than any other sleep disorder. Sleep apnea is characterized by recurrent failures to breathe adequately during sleep (termed apneas or hypopneas) as a result of obstructions in the upper airway.

Apnea is typically defined as a complete cessation of airflow. Hypopnea is typically defined as a reduction in airflow disproportionate to the amount of respiratory effort expended and/or insufficient to meet the individual's metabolic needs. During an apnea or hypopnea—commonly referred to as a respiratory event—oxygen levels in the brain decrease while the carbon dioxide ($CO_2$) levels rise, causing the person sleeping to awaken. The heart beats rapidly and blood pressure rises to levels (up to 300 mm Hg). The brief arousals to breathe are followed by a return to sleep, but the apneas may recur over 60 times per hour in severe cases.

Sleep apnea is a serious, yet treatable health problem for individuals worldwide. Published reports indicate that untreated sleep apnea patients are three to five times more likely to be involved in industrial and motor vehicle accidents that have impaired vigilance and memory. Studies show that more than 15% of men and 5% of women over the age of 30 and up to 30% of men and women over the age of 65 suffer from sleep apnea. Sleep apnea during pregnancy is associated with hypertension and a risk of growth retardation in the fetus. Current estimates reveal that over 90% of individuals with moderate to severe sleep apnea remain undiagnosed.

The current standard for the diagnosis of sleep apnea is called polysomnography (PSG), which is administered and analyzed by a trained technician and reviewed by a Board Certified Sleep Specialist. The limited availability of sleep centers coupled with the high capital expense, in order to add capacity for diagnosis of sleep disorders, has resulted in a growing number of patients awaiting analysis by polysomnography.

A conventional full overnight PSG includes recording of the following signals: electroencephalogram (EEG), submental electromyogram (EMG), electroculogram (EOG), respiratory airflow (oronasal flow monitors), respiratory effort (plethysmography), oxygen saturation (oximetry), electrocardiography (ECG), snoring sounds and body position. These signals are considered the "gold standard" for the diagnosis of sleep disorders in that they offer a relatively complete collection of parameters from which respiratory events may be identified and sleep apnea may be reliably diagnosed. The RR interval, commonly referred to as beats per minute, is derived from the ECG. The body position is normally classified as: right side, left side, supine, prone, or up (e.g., sitting erect). Typically, a microphone is taped over the pharynx and the body position sensor is attached over the sternum of the patient's chest. Each signal provides some information to assist with the visual observation and recognition of the respiratory events.

A collapse of the upper airway is identified when the amplitude of the respiratory airflow and the effort signals decrease by at least 50%, snoring sounds either crescendo or cease, and oxygen desaturation occurs. A respiratory event is confirmed (i.e., desaturation not a result of artifact) by the recognition of an arousal (i.e., the person awakens to breathe), typically identified by an increase in the frequency of the EEG, an increase in the heart rate or changing in snoring patter. The remaining signals assist in determining specific types of respiratory events. For example, the EEG and EOG signals are used to determine if a respiratory event occurred in non-rapid eye movement (NREM) or rapid eye movement (REM) sleep. The position sensor is used to determine if an airway collapse occurs only, or mostly, in just one position (typically supine).

A reduction or absence of airflow at the airway opening defines sleep-disordered breathing. Absent of airflow for 10 seconds in an adult is apnea, and airflow reduced below a certain amount is a hypopnea. Ideally one would measure actual flow with a pneumotachygraph of some sort, but in clinical practice this is impractical, and devices that are comfortable and easy to use are substituted. The most widely used are thermistors which are placed in front of the nose and mouth to detect heating (due to expired gas) and cooling (due to inspired air) of a thermally sensitive resistor. They provide recordings of changes in airflow, but as typically employed are not quantitative instruments. Currently available thermistors are sensitive, but frequently lag or have a delay in response time relative to pressure sensors and pressure transducers. Also, if they touch the skin, they cease being flow sensors. Measurement of end tidal CO, is used in some laboratories to detect expiration to produce both qualitative and quantitative measures of a patient's breath.

An alternative method is to measure changes in pressure in the nasal airway that occur during breathing. This approach provides an excellent reflection of true nasal flow. A simple nasal cannula attached to a pressure transducer can be used to generate a signal that resembles one obtained with a pheumatachygraph. It allows detection of the characteristic plateau of pressure due to inspiratory flow limitation that occurs in subtle obstructive hypopneas.

An obstructive apnea or hypopnea is defined as an absence or reduction in airflow, in spite of continued effort to breathe, due to obstruction in the upper airway. Typical polysomnography includes some recording of respiratory effort. The most accurate measure of the effort is a change in pleural pressure as reflected by an esophageal pressure monitor. Progressively more negative pleural pressure swings, leading to an arousal, have been used to define a "Respiratory Effort Related Arousal" (RERA), the event associated with the so-called "upper Airway Resistance Syndrome". However the technology of measuring esophageal pressure is uncomfortable and expensive, and rarely used clinically. Most estimates of respiratory effort during polysomnography depend on measures of rib cage and/or abdominal motion. The methods include inductance or impedance plethysmography, or simple strain gages. Properly used and calibrated, any of these devices can provide quantitative estimates of lung volume and abdominal-rib cage paradox. However, calibrating during an overnight recording is very difficult and, as a practical matter, is almost never done. The signals provided by respiratory system motion monitors are typically just qualitative estimates of respiratory effort.

Pressure sensing devices are currently available and used during a sleep diagnostic session to detect changes in respiratory air pressure and/or airflow to confirm whether or not a patient is breathing and to gather other breathing information from the patient. Accurate modeling of the patient's breathing cycle is limited by the use of only pressure sensors as the placement of sensors and system failures can cause false readings or pressure offsets that must be adjusted to properly model the breathing cycle.

Combining pressure sensor measurements with temperature sensor measurements can improve breath monitoring and modeling thereby leading to a more accurate diagnosis and more quickly determine a patient's breathing failure by utilizing temperature monitors directly positioned at the nasal and oral breathing passages of the patient. Additionally, in using a temperature sensor for breath monitoring, it is generally necessary to test the electrical leads and circuit components of the temperature sensing device to insure that all of the electrical leads and components are, in fact, operational and not faulty.

In addition, conventional test circuitry typically is completely separate from the temperature sensing device and this leads to further difficulties such as the test circuitry being either misplaced, lost, having insufficient electrical power, etc., thereby rendering it difficult to test the pressure sensing device prior or during use.

SUMMARY OF THE INVENTION

It is an object of the invention to provide a system including an apparatus and method for monitoring patient breathing through a temperature sensor and pressure sensor adapted for use with a nasal and oral cannula.

It is a further object of the invention to provide a method of securing a temperature sensor to a nasal and oral cannula such that the temperature sensor can be positioned directly at the outlet of the nares of the patient's nose and adjusted to properly position the sensors directly in the air flow from the patient's mouth and nose and out of contact with the patients skin.

Another object of the invention is to provide an electronic circuit for the temperature sensors that includes a test circuit for determining the continuity of the temperature sensor circuit as a whole. The electronic circuit also has connections to an external microprocessor or controller to measure and accurately model a patient's breathing patterns based on the temperature and pressure data so as to provide a diagnosis for sleep apnea or, alternatively, to provided a basis for a determining proper gas and oxygen delivery to a patient.

Another object of the present invention is to facilitate ease of use of a coupled nasal cannula and temperature sensing device whereby the temperature sensing device mounts securely to a portion of the cannula and the structure of the mount and temperature sensing device permits relative adjustment of the sensors into position to properly align with the patient's nasal and oral expiration and inspiration, i.e., air flow.

Another object of the present invention is to provide test circuitry which is integrated directly into the signal temperature sensing device and readily allows the temperature sensing device to be quickly and conveniently tested, prior to and during use of the temperature sensing device, and includes a visual or audible indicator which indicates the continuity of the circuit the test circuit but does not continuously use power except when actuated by a user to test the circuit.

Yet another object of the present invention is to provide test circuitry in which the integrity of all of the internal circuitry of the temperature sensing device can be quickly and conveniently checked, by utilizing an internal battery powered circuit, to insure that there is adequate electrical conductivity for all of the internal circuitry and that none of the internal circuits are open, e.g., no electrical short is contained within any of the internal circuits.

The present invention relates to an airflow and temperature sensing device adaptive to a cannula for receiving respiratory breathing information from a patient to be monitored, the temperature sensing device comprising: a nasal breath monitor and an oral breath monitor configured as a series of thermistors inserted within an insulating sleeve and arranged in a T-shape form so as to adapt to connection with the rounded tubular surface of a nasal and oral cannula. Each thermistor is a temperature sensing device and is connected to wire leads that exit the insulating sleeve at each extension of a nares support frame within the nasal breath monitor. The T-shaped sensor configuration includes a right frame branch and a left frame branch that each extend from opposing sides of a central point to form an adjustable nares bridge. The nares bridge is flexible and allows movement of each of the branches in essentially a 360 degree freedom of movement range to facilitate proper alignment of the thermistors, mounted within each branch, with the nasal air flow of the patient for proper monitoring.

An oral support branch extends from the central point to form the oral breath monitor. An oral temperature sensor is mounted within the oral support branch but spaced from the adjustable nares bridge. Manipulating the adjustable oral branch the oral sensor can be moved axially or laterally, i.e., 360 degrees to properly align the oral temperature sensor with the oral breath of the patient for proper monitoring.

In one embodiment of the invention, each temperature sensor is a thermistor with negative temperature coefficient characteristics that exhibits a decrease in electrical resistance as temperature increases and increase in electrical resistance as temperature decreases. Changes in temperature within a range of 1° C. to 2° C., and more preferably within a 1° C., will change the resistance of the thermistor sensor and cause an increase or decrease in current within an external temperature sensor or respiratory airflow detection circuit. By attaching the temperature sensor to a nasal and oral cannula with the use of a special mounting holster integrated within the cannula, the breathing cycle of a patient can be monitored. On exhalation by the patient there will be an increase temperature of the air immediately at the base of the nasal outlet or nares and at the oral outlet of the mouth. This increase in temperature will decrease the resistance of the temperature sensor thermistors causing an electrical change within the respiratory airflow detection circuit. According to one embodiment, this electrical change creates a change in frequency within a capacitive filter circuit generating a signal emission that is read by a microprocessor that tracks the amplitude and frequency of each thermistor resistance change. Each exhalation and inhalation of the patient is directly tracked by the close proximity of the temperature sensor to the nares and oral cavity of the patient.

Temperature modeling of the breathing cycle could supplement the commonly used pressure sensor breath cycle modeling to better indicate aberrations within the cycle and more reliably track changes that are related specifically to the breathing physiology of the patient and not external limitations of the monitoring system. Temperature sensors directly at the patient's nose and mouth more accurately detect changes and more quickly detect any stoppage of breathing by the patient providing for the use of the external resistance change for activating an alarm signal to indicate the patient is in distress.

The use of sensors for monitoring breathing of a patient requires that the circuitry within the system be operational and free from faults prior and during use. The present invention includes test circuitry that identifies faults in the thermistors, the thermistor leads and the internal circuit components of the respiratory airflow detection circuit. No external test equipment is required to safely and easily test if the leads are free from any short(s) or open(s) and to determine that the thermistors and other circuitry components are operational. In one embodiment, the external leads from the thermistors and nares support frame are connected to test circuitry that can be activated to test continuity and powered operation within the system by pressing a test button and visually acknowledging an LED indicator to confirm that the circuit operation is properly functioning. The failure of the LED to illuminate indicates a system fault that must be investigated prior to use of the temperature sensing device.

The present invention relates to a temperature sensing device for coupling to a cannula and receiving respiratory breathing information from a patient to be monitored. The temperature sensing device has an internal test circuit for testing an integrity of all electrical leads and circuit components prior to use for ensuring that the temperature sensing device is operational.

The present invention also relates to a method of using a cannula to receive respiratory breathing information from a patient to be monitored, the method comprising the steps of: using a temperature sensing device comprising a support frame with adjustable bride supports and temperature sensors mounting along to support frame for receiving the respiratory breathing information from the patient to be monitored; processing the received respiratory breathing information from the patient and outputting, a signal indicative of the sensed breathing cycle of the patient; accommodating a respiratory airflow detection circuit within an exterior housing for processing the received respiratory breathing information from the patient and outputting, a signal indicative of sensed airflow of the patient; and testing an integrity of the electrical leads, temperature sensors and circuit components via an internal test circuit, prior to use of the temperature sensing device, to ensure that the temperature sensors for breath monitoring are operational.

BRIEF DESCRIPTION OF THE DRAWINGS

The invention will now be described, by way of example, with reference to the accompanying drawings in which:

FIG. 13A is a diagrammatic front elevational view of a third embodiment of a cannula supporting a temperature sensor;

FIG. 13B is a diagrammatic top plan view of FIG. 13A showing engagement of the cannula with the temperature sensor;

DETAILED DESCRIPTION OF THE INVENTION

Figure 1:
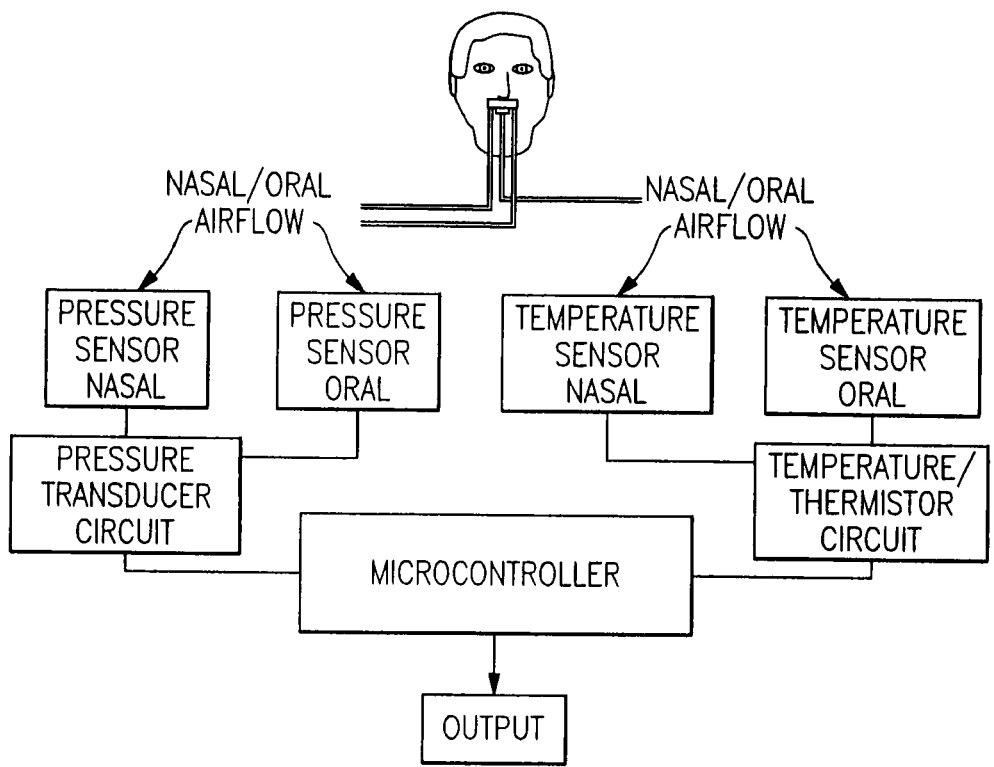
FIG. 1 is a flow diagram representation of the present invention within a breath monitoring system.

The present invention is directed to an apparatus and method for monitoring and modeling a patient's breathing according to both pressure and temperature measurements. As seen in FIG. 1, from oral and nasal airflow of a patient oral and nasal temperature measurements are obtained according to temperature changes measured by a thermistor during the exhalation and inhalation interval of a patient during a sleep diagnostic session. A temperature sensor—generally a thermistor although other types of thermocouples and temperature sensors could be used as well—is positioned adjacent the nares (nostrils) of the patient's nose (nasal temperature sensing) and adjacent the patient's mouth (oral temperature sensing). An output signal, from the temperature sensor(s), is conditioned by a thermistor circuit and sent to a micro controller to be processed into acquired air wave and airflow breathing data for input to conventional polysomnography equipment which produces an output representation of the patient's breathing cycle generally as a qualitative, viewable waveform.

A pressure sensor is also used in the system in conjunction with the temperature sensor. The pressure sensor—like the thermistor—is a non-invasive alternative for measuring nasal and oral airflow of a patient during the diagnostic study. A pressure sensor is generally the preferred method of determining nasal air flow since the nasal prongs of the cannula are situated essentially inside the nares of the patient's nose and directly in the flow path of nasal inspiration and expiration. It follows that nasal pressure sensing, often achieved with a pressure transducer, is generally a more accurate method of assessing hypopneas in real time, which is critical to the accurate diagnosing of a patient.

If a patient breaths through his or her mouth, on the other hand, it is more difficult to obtain an accurate pressure measurement based on inspiration and expiration through the mouth. Because of the size of a patient's mouth in general, it is difficult to align an oral prong or cannula opening at an appropriate position to obtain the oral inspiration and expiration. For example, a person may breath out the side of their mouth and thus an oral prong, located in the center of the mouth for pressure sensing, may not receive adequate breathing flow to properly determine pressure. In the case of a mouth breather like this, the temperature sensor with an oral thermistor may provide the best response using the temperature differential between the ambient air and whatever portion of the patient's breathing is obtained.

To determine an accurate wave form of the patient's breathing, a nasal cannula is generally used by the patient which is then connected to a pressure sensor, for example, a sensitive pressure transducer. The pressure transducer emits a signal which is proportional to the flow and this signal is processed, by the micro controller, to generate a respiratory waveform signal which indicates the fluctuations in pressure caused by inspiration and expiration of the patient. In the present system, a temperature sensor may also be used with the cannula, or mask in the case of titration, to provide further accuracy in determining breathing cycle data and an accurate wave form.

In general, and as discussed in further detail below, in order to most effectively determine an actual accurate wave form including the most accurate amplitude as well as frequency, i.e., breaths per minute, the present embodiment of the system includes a thermistor(s), as the temperature sensor for obtaining the oral and nasal temperature changes of a patient's inspiration and expiration, which is adapted to be affixed to a nasal and oral cannula. The cannula is used, as described above, to obtain the nasal and oral airflow and derived pressure changes in the patient's breathing which, along with the data obtained by the thermistor, can then be compared to obtain the most accurate waveform and most precise monitoring and diagnosis of a patient's respiratory airflow and breathing cycles including confirmation of distress signals from hypopneas or apnea events.

FIG. 1 is a basic flow chart of an embodiment of a temperature and pressure sensor breath monitoring system for providing conformational data of changes or aberrations within a patient's breathing cycle from a nasal pressure sensor and oral pressure sensor as well as a nasal temperature sensor and oral temperature sensor. The attachment of the temperature sensor and thermistors to the cannula ensures that the thermistors are located adjacent the oral and nasal passages of the patient to obtain an accurate temperature change in concurrence with the nasal and oral inlets of the cannula which receive the air flow indicative of pressure changes which effect the pressure sensor. The nasal pressure sensor is provided in conjunction with the oral pressure sensor, via the cannula, to provide a pressure signal to the microcontroller, and the nasal temperature sensor along with an oral temperature sensor, via a thermistor, is connected to the microcontroller to supply a further temperature change signal to the microcontroller. This system therefore provides a pressure and temperature signal from each breathing cycle to the microprocessor or controller and can be accumulated, processed and provided as a breathing pattern output for diagnosis and treatment purposes.

Figure 2:
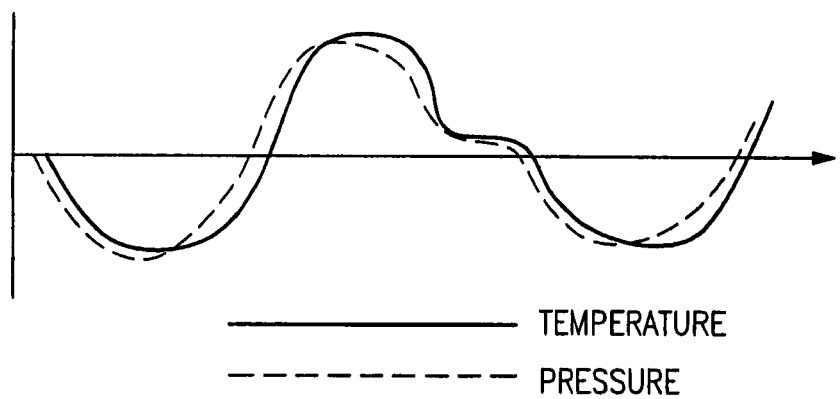
FIG. 2 is a graph illustrating a flow rate profile of the breathing cycle of a patient combining pressure sensor and temperature sensor data.

FIG. 2 shows an example of a breathing pattern output derived from the acquired temperature and pressure data of the patient's breathing cycle. Pressure data is collected from the cannula and the pressure sensor, on the one hand, and temperature data, on the other, is also collected from the oral and nasal temperature sensors over a period of time to track the patient's breathing cycle. When both the pressure and temperature sensors are plotted together, as shown in FIG. 2, it becomes apparent, despite any lag time in the temperature measurement and response, where potential anomalies or errors may exist in the respective temperature and pressure sensors and signals, and also that the system can more reliably detect apnea, hyopopnea and other subtle flow limitations where both pressure and temperature signal outputs can be concurrently determined from a patient's baseline oral and nasal breathing pattern.

Figure 3A:
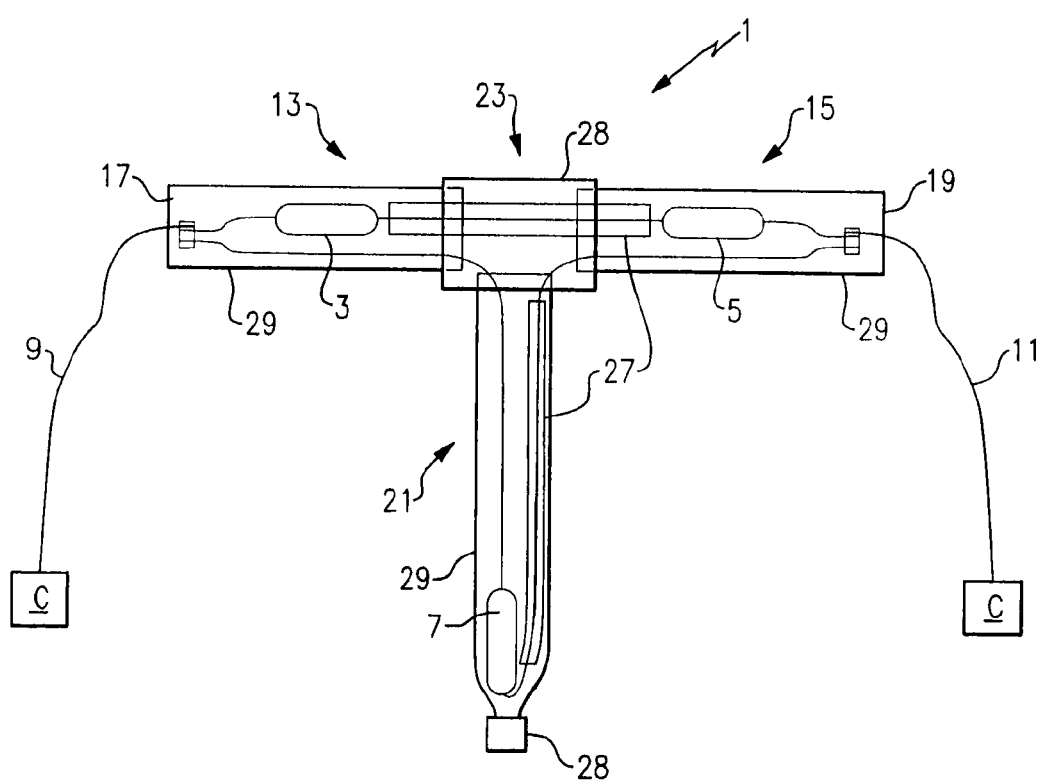
FIG. 3A is a diagrammatic representation of the temperature sensor of the present invention.
Figure 3B:
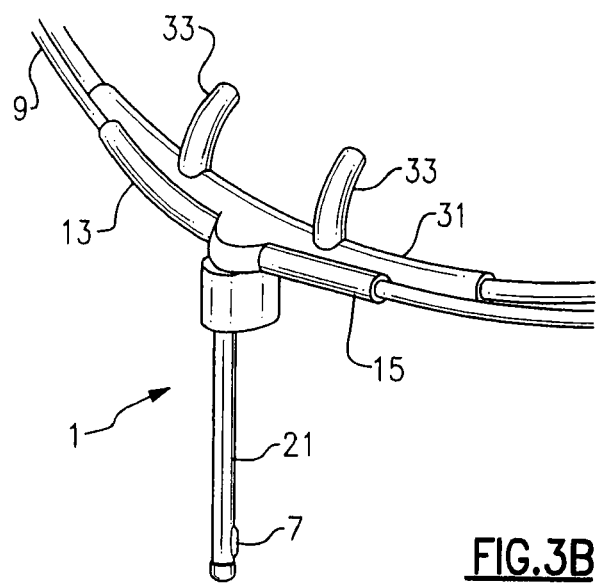
FIG. 3B is a perspective view of an embodiment of the pressure and temperature sensor mounted together without an oral pressure sensing prong.
Figure 3C:
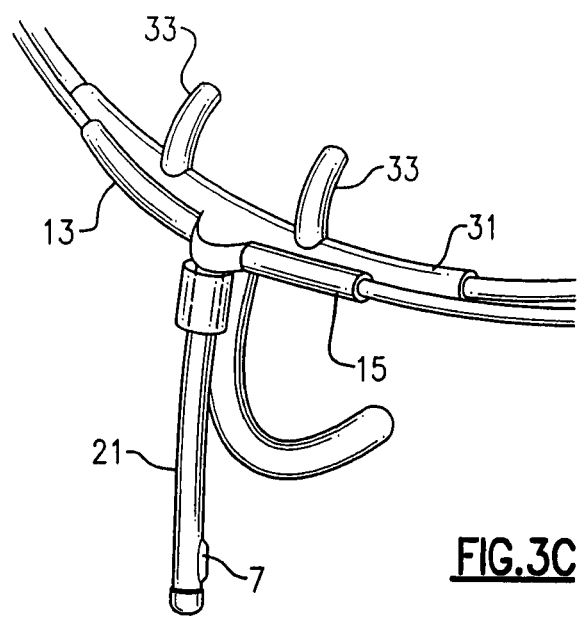
FIG. 3C is a perspective view of an embodiment of the pressure and temperature sensor mounted together with an oral pressure sensing prong.

Turning now to FIGS. 3A, 3B and 3C, the temperature sensor 1 of the embodiment shown here is a triad, i.e., three thermistors 3, 5 and 7 comprising a first nasal thermistor 3 in series with a second nasal thermistor 5 on a nasal circuit, and an oral thermistor 7 that is positioned along an oral circuit connected in parallel and structurally aligned perpendicular to the nasal circuit of the first and the second nasal thermistors 3 and 5. First and second leads 9 and 11 are connected to the respective circuit junctions of the nasal and oral circuits to send the resistivity change to a conditioning circuit C, described in further detail below.

The temperature sensor 1, including the thermistors, is formed in a T-shaped configuration with the first nasal thermistor 3 located in a left branch 13 of the sensor 1. The second thermistor 5 positioned in the right branch 15 of the sensor 1, and the oral thermistor 7 located in the lower branch of the T-shaped sensor. When properly positioned on the cannula and on the face of a patient, the left and right branches 13, 15 extend in each lateral direction under the nasal septum of the patient's nose toward respective free ends 17, 19 so that each of the nasal thermistors 3, 5 are positioned directly adjacent the opening to each respective left and right nares of the patient's nose The left and right branches 13, 15 form a rigid but flexible bridge that provides structurally stable and flexible support to allow for each of the left and the right branches 13, 15 to be adjusted, i.e., bent, manipulated, curved or articulated into a desired position relative to one another and relative to the oral thermistor 7. Although the branches are shown here as being linearly aligned, the flexibility of the branches 13, 15 permits non-linear alignment as can be seen in subsequent figures. This non-linear flexibility facilitates aligning and maintaining the respective right and left nasal thermistors 3, 5 with the patient's right and left nares and does so in conjunction with the nasal prongs of the cannula supporting the temperature sensing device inlets. It is also to be appreciated that there does not necessarily have to be two thermistors 3, 5 in the bridge, e.g., that there could only be a single thermistor located in the bridge which could be aligned with one of nostrils of the patient or possibly at a location between the nostrils of the patient or could be aligned with one of the nares of the cannula or possibly between the T-nares of the cannula.

Similarly, a lower branch of the T-shaped sensor extends perpendicularly downwardly relative to the flexible bridge and is also adjustable, flexible and manipulatable such that the lower branch 21, which includes the oral temperature circuit and oral thermistor 7, provides the same rigidity and rnaleability to structurally support the oral thermistor at a desired orientation or position adjacent the patient's mouth. In the case of each branch 13, 15 and 21, the branches can independently arranged with respect to one another about the center joint 23. In other words, each branch is radially flexible in a 360 rotational manner about the center joint 23, and each branch is also axially flexible, i.e., bendable along its longitudinal axis to ensure that the oral thermistor 7 is not only placed in an appropriate position adjacent the patient's mouth so that it is fully located in the path of inspiration and expiration, but also can be adjusted so as not to touch any part of the patient's mouth, tongue, skin or face.

The T-shape configuration of the temperature sensor 1 is important because, by its very nature, the T-shape defines three (3) independent branches 13, 15 and 21 which extend from a center joint 23 to three (3) free ends. The left and right upper branches each define a left and right free end 17, 19 and the depending prong 29 also defines its own respective lower free end. With each branch extending from the center joint 23 in this manner to the respective free ends 17, 19 and 25, each branch 13, 15, and 21 along with the associated thermistor 3, 5 and 7 can consequently be independently adjusted, bent and/or configured to a desired shape or configuration independent of one another. By way of example, the left and right branches 13, 15 may be bent in a manner to curve laterally in cooperation with the curved shape of the cannula or the curved skin and face surface of the patient, as can be seen in FIGS. 3B and 3C. This allows each thermistor in the sensor to be directly aligned in the flow path of the nasal airflow passing through the patient's nares. Similarly, but independently of the left and right branches 13, 15, the lower branch 21 may be curved, bent or manipulated so as to most effectively position the oral thermistor 7 in the most advantageous position to receive the oral temperature change from the patient's oral airflow. Also, by appropriately arranging the lower branch 21 independent of the left and the right branches 13, 15, it can be assured that the lower branch 21 and the oral thermistor 7 does not contact the patient's skin or mouth and thereby adversely influence the response of the thermistor to the oral airflow of the patient.

This independent flexibility of the lower branch 21 is critical because if the oral thermistor 4 touches the skin or face of the patient, the thermistor will be effected by the body and skin temperature in addition to any temperature changes caused by the patient's breathing. Also, the ability to bend and manipulate the lower branch 21 in what is essentially a 360 degree manner ensures that the oral thermistor 7 can be placed in the most direct path of the patient's inspiration and expiration airflow. While the flow path of inspiration and expiration generally does not vary significantly through the nares or nostrils of the nose, because of the relative smaller size of the nare openings as compared to the mouth and the flow rate of a patient's breathing, the mouth is much larger than the nares and a patient may breath out the side, top or bottom of his or her mouth. Thus, the ability to radially and axially articulate and maintain the lower branch 21, and hence the oral thermistor 7, in a region where the patient's most direct oral inspiration and expiration is occurring is critical to obtaining an appropriate and accurate reading and response of oral expiration and inspiration. This rigid flexibility of the temperature sensor and adjustments thereof relative to the nares and mouth permits proper positioning and configuring of the temperature sensor to align and match the proper physical characteristics of patients independently of the nasal and oral prongs of the cannula to which the sensor 1 is attached.

Figure 3D:
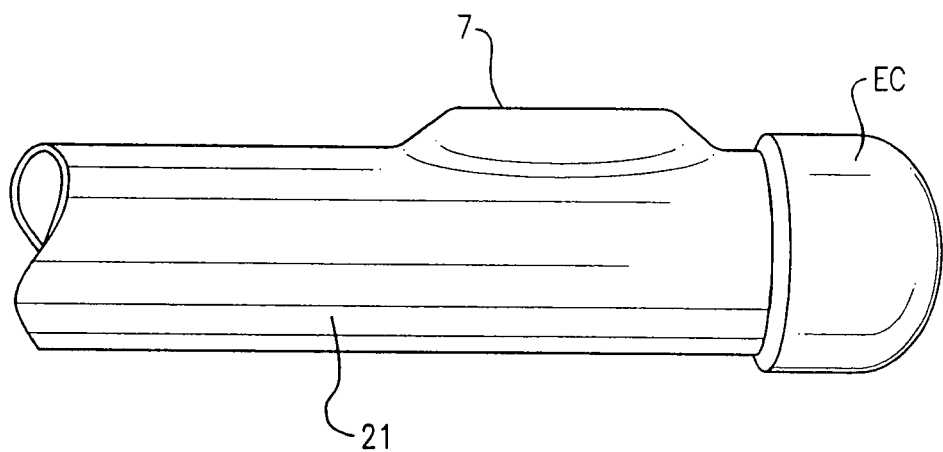
FIG. 3D is an enlarged perspective view of a free end a lower branch a T-shaped sensor which is provided with an exterior surface which tends to be ejected or forced out of or away from the mouth, gums and/or teeth of a young child or infant in the event that such patient attempts to suck, bite or chew on the same.

In the arrangement shown in FIG. 3D, it is to be appreciated that the two thermistors 3, 5 are located adjacent the nasal prongs 33, 33 while the third thermistor 7 is supported by the lower branch 21 and can be suitably positioned or adjusted to a location so that the third thermistor 7 can be located directly in the flow path of the air being exhausted from the mouth of a patient. In the event that the patient is a young child or an infant, for example, such child or infant may be prone to either suck, bite and/or chew on the remote free end of the lower branch 21 and/or the thermistor 7 since the free end of the lower branch 21 is positioned adjacent the mouth of such patient. To avoid or minimize as much as possible this tendency, the free or leading end of the lower branch 21 generally terminates in teardrop shaped end or, alternatively, the free end of the lower branch 21 may be provided with an end cap EC which has an exterior surface which is teardrop shaped, or suitably shaped or contoured, so that the free or leading end of the lower branch 21 tends to be ejected or forced out of or away from the mouth, gums and/or teeth of a young child or infant in the event that such patient attempts to suck, bite and/or chew on the same. Due to the modified exterior shape or contour of the free or leading end of the lower branch 21, such shape does not provide any flat or cylindrical or other surfaces or areas which can be easily and readily be grasped by the gums, teeth and/or mouth of a young child or infant and this minimizes the possibility that the young child or infant will be able to captively retain the free end of the lower branch 21 in his/her mouth for an extended period of time during use. That is, the exterior profile or contour of the cap EC or the free or leading end of the lower branch 21 is designed, e.g., is generally rounded, curved or tapered, to bias the thermistor 7 away from the mouth of such young child or infant so that the thermistor 7 can remain in the path of the air flow being exhausted from the mouth of such young child or infant and still effectively operate to sense temperature of the air being exhaled.

It is to be appreciated that the end cap EC can either be integrally formed with the free end of the lower branch 21 or be affixed thereto following manufacture of the T-shaped sensor by a conventional adhesive.

Figure 4A:
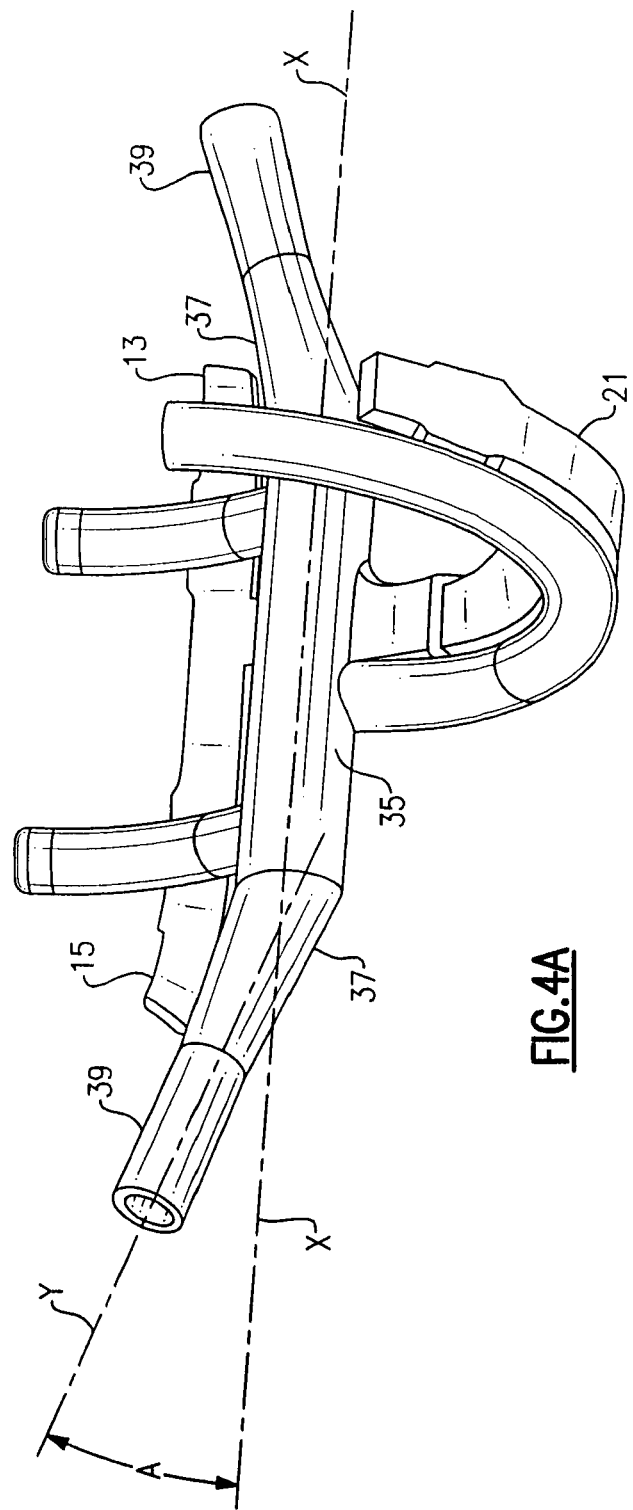
FIG. 4A is representation of the cannula and temperature sensor and associated initial arm angle of the appertaining arms of the cannula.
Figure 4B:
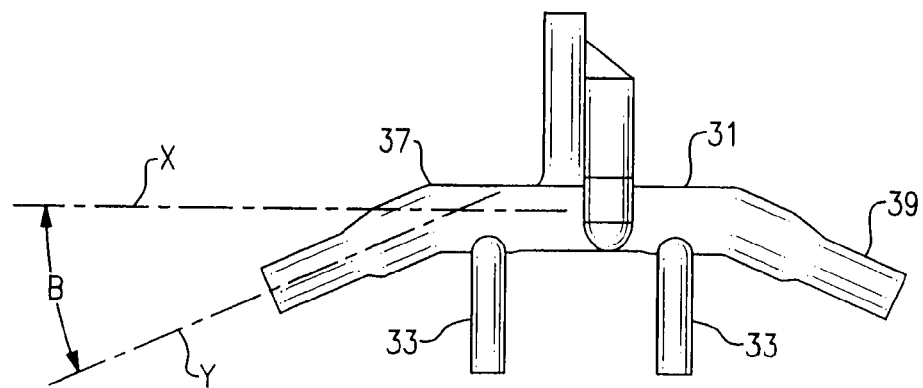
FIGS. 4B and 4C are representations of the cannula and temperature sensor and associated adjacent angles of the appertaining arms of the cannula.
Figure 4C:
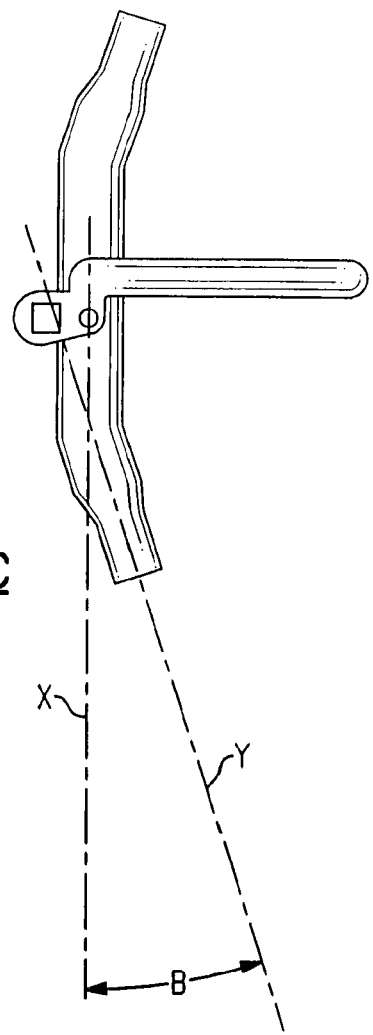

The ability to independently position the branches 13, 15 and 21 relative to the fixed orientation in which the center joint 23 of the temperature sensor 1 is held with respect to the cannula is also important in regards to the shape of the cannula 31 and the cannula body 32. In an embodiment of the present invention, the cannula body 35 extends for a portion of its length along a main x-axis, as can best be seen in FIGS. 4A, 4B and 4C. Elbows 37 are formed at either end bending in a 3-dimensional sense to define opposed arms 39 extending along a y-axis. As explained more fully in U.S. Pat. No. 4,106,505, the teaching of which is incorporated herein by reference, the y-axis extending along the length of each arm 39 intersects a horizontal plane defined by the x-axis of the main body 35 at an acute angle A from above the horizontal plane, as can be seen in FIG. 4A. In FIGS. 4B and 4C, the forward extension of the arms 39 (towards the patient's face) defines an acute angle B of intersection between the y-axis and horizontal x-axis. The independent flexibility of each branch 13, 15 and 21 of the temperature sensor 1 ensures that the branches may be suitably positioned, and retained in such a position, where the branches not only conform to this described shape of the cannula body 35 but also where the nasal and oral thermistors 3, 5 and 7 can be best positioned relative to the cannula to receive the necessary airflow while still avoid touching the patient's face.

It is to be appreciated that not all the branches 13, 15 and 21 are necessarily the same length. For example as discussed in further detail below, the temperature sensor 1 may be offset from a centerline of the cannula so that the left and the right branches 13, 15 might have different lengths relative to the center joint 23 of the sensor 1 to properly position the respective thermistors 3 or 5 adjacent the nasal prongs 33 and in the patient's nasal airflow. Alternatively, where the branches 13, 15 are the same length, the thermistors may be spaced different distances from the center joint 23 of the sensor 1 so that they are aligned adjacent the nasal prongs 33 and in the nasal air flow of the patient. Typically, the lower branch 21 is longer than the upper branches 13, 15 to extend from the center joint 23 to an appropriate position in the oral airflow of the patient.

The nasal and oral thermistors 3, 5 and 7 and their respective circuits and wire leads 9, 11, shown in FIG. 3A, may be joined in any manner known in the art for example by soldering, taping, brazing or welding and may be protected and insulated by applying an inner layer of heat-shrink tubing 27 to protect and insulate these joints and connections from the external environment. An outer layer of heat shrink material 29 may be applied over the circuits, joints, leads and thermistors as well to provide some level of insulation from the environment, without degrading the response of thermistors and circuits. Also, any portion(s) of the temperature sensor circuit not covered by the heat shrink material may be sealed with a non-conductive sealant or fixative, for example, a silicone polymer generally depicted as layer 28, or some such similar non-conductive material to entirely seal the temperature sensor circuit from contact with ambient air. The center joint 23 of the T-shaped temperature sensor 1 may, for example, be sealed with the layer 28 to provide not only sealing and insulation of the circuit, but also define a relatively rigid reference point from which each of the left and the right branches 13, 15 and the lower branch 21 extend and can be independently adjusted relative thereto.

The airflow temperature sensor 1 can be a negative temperature coefficient (NTC) thermistor which exhibits decreasing electrical resistance with an increase in environmental temperature and increasing electrical resistance with a decrease in environmental temperature. By way of example, the thermistors 3 and 5 of the nasal temperature circuit shown in FIG. 3A may have a resistance of 5 k each, while the oral thermistor 7, arranged in parallel, may have a 10 k resistance. In another embodiment, all the thermistors could be arranged in series as 10 k resistance, particularly where a more substantial power supply is provided besides a small DC battery, discussed with respect to FIG. 5 below. A larger power supply would permit higher resistance to be used through the circuit and thus a greater range of responsiveness for any temperature differential.

Figure 5:
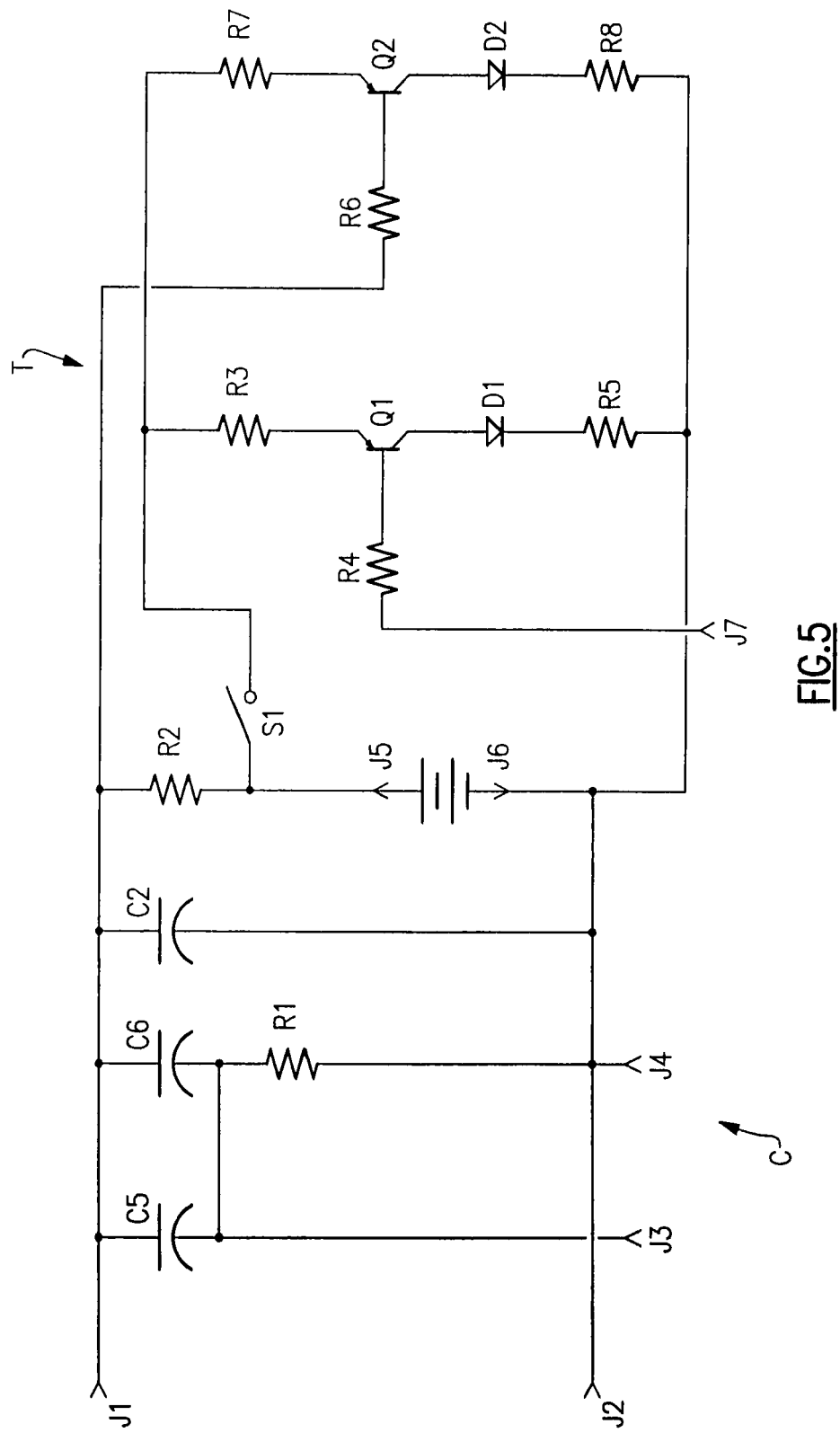
FIG. 5 is a circuit schematic diagram of the respiratory airflow detection circuit with test circuitry for testing the operational functionality of the temperature sensor.

As discussed above, the left external lead 9 and the right external lead 11 of the temperature sensor 1 are connected to a respiratory temperature detection circuit C having a test circuit as shown in FIG. 5. The respiratory airflow detection circuit C determines the change in temperature across the thermistor(s) based on the proportional change of a voltage divider in the circuit. The test circuit T ensures that the continuity of the circuit is maintained and can be monitored and readily ascertained, at any desired time, by merely depressing a button and without maintaining a diode or indicating light on at all times.

As can be seen in FIG. 5, which is a schematic of the respiratory temperature detection circuit, the left external lead 9 is coupled as an input at J1 and the right external lead 11 is coupled as an input at J2. Power is applied to the circuit via a battery, for example a 3 volt coin cell connected to J5 (Pos) and J6 (Neg). Thermally equilibriating a change in temperature across the thermistors in the temperature sensor 1 will cause the voltage divider voltage to change proportionally with temperature at the junction of R2 and the thermistor lead terminal J1. If the rate of change in temperature is within a passband, then the voltage can be measured at the head box leads.

The resistors and capacitors form a band pass filter with the combination of R2 and C2 forming a low pass filter with a cutoff frequency of around 42 Hz and the combination of C5 plus C6 and R1 form the high pass filter with a cutoff frequency of around 0.066 Hz.

The capacitors C5 and C6 with resistor R1 and the resistive inputs of the temperature sensors through J1 and J2 form a filter capacitive circuit that generates frequency changes as the resistance changes within the thermistors of the temperature sensors on each inhalation and exhalation of the patient's breathing cycle. An output analog signal is generated and fed, via connections J3 and J4, to a microprocessor or other controller to model the patient's breathing cycle or to compare the signal to other breath monitors such as a pressure sensor output of oral or nasal breath, as shown in FIGS. 1 and 2.

FIG. 5 also includes the test circuit T that tests the integrity of lead lines 9 and 11, connected to J1 and J2, and the internal circuit components of the respiratory airflow detection circuit. The test circuit T includes a switch S1 that, when closed, creates a closed circuit for all components. Power is applied to the transistors circuits when the switch S1 is temporarily closed. A first LED D1 will illuminate if a white or black head box lead is plugged into the J7 lead tester jack and S1 is closed verifying the integrity of the head box lead. A second LED D2 will illuminate when S1 is closed verifying the integrity of the thermistor leads. Any failure within the leads, the connections or the circuit components will fail to illuminate at least one of the test indicators, D1 or D2, and this identifies to the operator a problem within the circuit.

Figure 6:
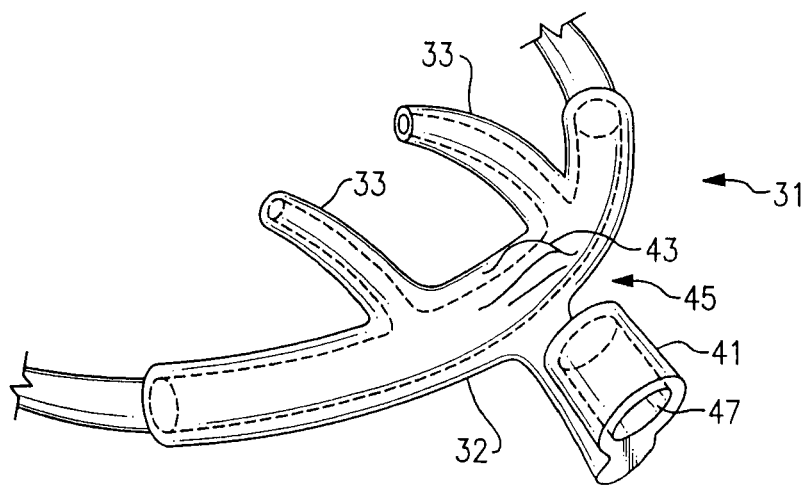
FIG. 6 is a front perspective view of a cannula of a first embodiment of the present invention used to support the temperature sensor.
Figure 7:
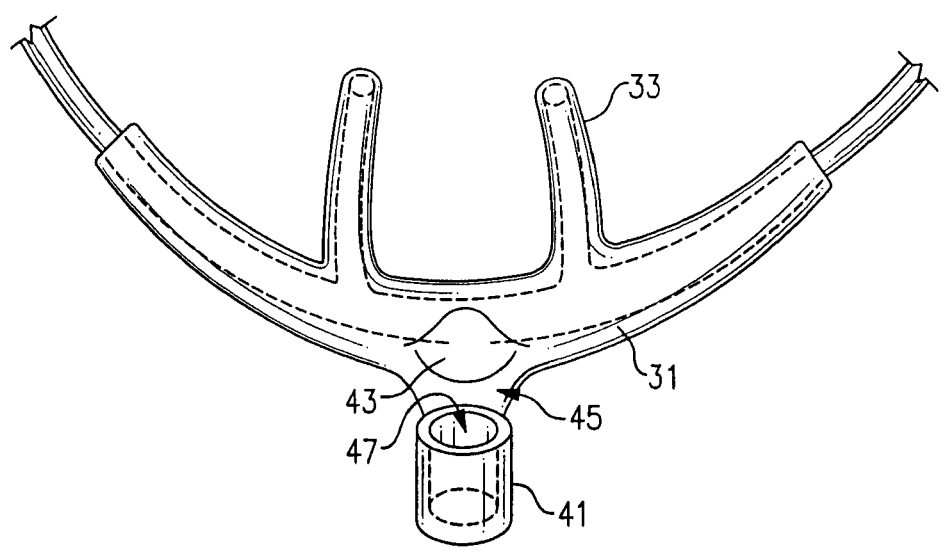
FIG. 7 is a rear view of the cannula of the first embodiment used to support the temperature sensor.
Figure 8:
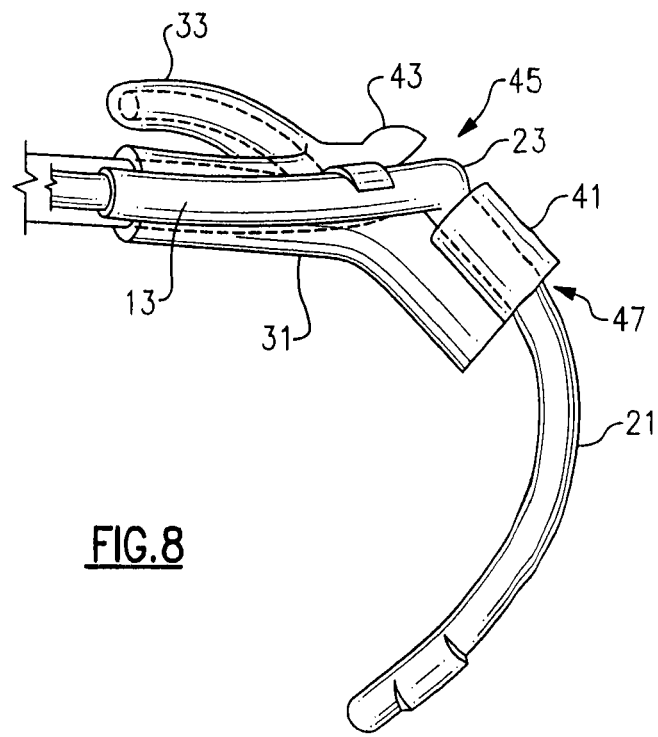
FIG. 8 is a side view of the cannula of the first embodiment used to support the temperature sensor via the holster of the cannula.

FIGS. 6, 7 and 8 show details a cannula 31 for use in the presently described system in conjunction with the above described temperature sensor 1 and the circuit C. The cannula 31 includes a main cannula body 32 which is hollow and has first and second ends defining respective openings through which air and/or gas are delivered or received generally through a pair of nasal prongs 33, as are well known in the art, for receiving exhalation gases and/or supplying oxygen to the patient. The cannula 31 of this embodiment is further provided with an integral receiving holster 41 and stop portion 43 which defines a receiving notch 45 therebetween. The holster 41 is integrally connected or formed with the body 32 of the cannula 31 and provided with a sensor passage 47. The sensor passage 47 may be of any desired shape, and does not even have to be entirely enclosed, i.e., formed as a cylinder, but is sized so as to receive a portion of the temperature sensor 1, namely, the lower branch 21 which is located within the passage 47 and is generally frictionally retained therein.

During assembly, the lower branch 21 is pushed into the sensor passage 47 so that the oral thermistor 7 passes into and through the passage 47 and extends out a bottom end of the passage 47 (see FIG. 8). The lower branch 21 is pushed through the passage 47 until the extension for the left and the right branches 13, 15 of the pressure sensor 1 abut a top end of the passage 47 and accordingly situate the center joint 23 of the T-shaped sensor snugly in the receiving notch 45 between the stop portion 43 and a top surface of the holster 41. The stop portion 43, which is also integrally connected with the body of the cannula 31, extends outward therefrom to approximately the same dimensions as the holster 41. The receiving space or notch 45, defined between the stop portion 43 and the top surface of the holster 41, thus closely receives and holds the center joint 23 but is sufficiently flexible to facilitate the insertion and removal of the pressure sensor 1 into the passage 47 of the holster 41.

Once the T-shaped temperature sensor 1, as can be seen in FIG. 3, is inserted into the sensor passage 47, the branches 13, 15 and 21 may be independently manipulated in order to provide the appropriate positioning, alignment and/or curvature to these branches and their free ends as necessary in order to facilitate the most reliable data collection position, as previously described.

With reference now to FIGS. 9-12, a further embodiment of a cannula 31', according to the present invention, will be described. This embodiment also includes a holster 41 and a stop portion 43 in combination with an oral airflow pressure sensing tube 51 which communicates, in addition to the nasal prongs 33, with the main body of the cannula 31'. An oral pressure sensing tube 51 is provided to be substantially centered on, or even slightly offset, relative to a centerline A of the cannula body and the nasal prongs 33 on the cannula 31' (see FIG. 11). In order to ensure that the oral sensing thermistor 7 is not blocked or obstructed by the oral pressure sensing tube 51 in any manner, the holster 41 and the stop 43, in this embodiment, are radially offset from both the cannula centerline A as well as a centerline of the oral pressure sensing tube 51. This offset separation ensures that when the lower branch 21 of the sensor 1 is inserted through and into the holster 41, the lower branch 21 extends along the side of the oral pressure sensing tube 51 and thus can be directly aligned adjacent the patient's oral airflow without being blocked or otherwise obstructed by the pressure sensing tube 51.

Figure 9:
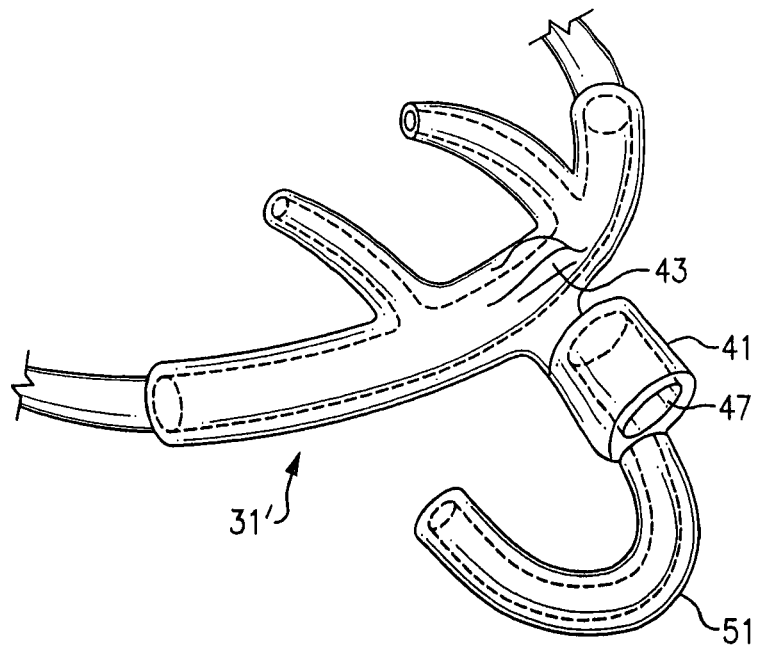
FIG. 9 is a perspective view of a second described embodiment of the cannula having an oral pressure sensing prong extending therefrom.
Figure 10:
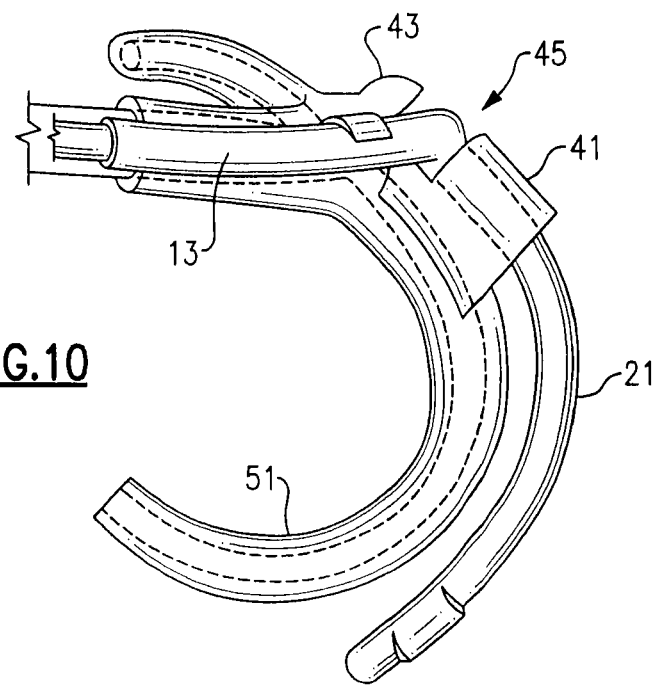
FIG. 10 is a side view of the cannula of the second embodiment of the invention used to support the temperature sensor shown therewith.
Figure 11:
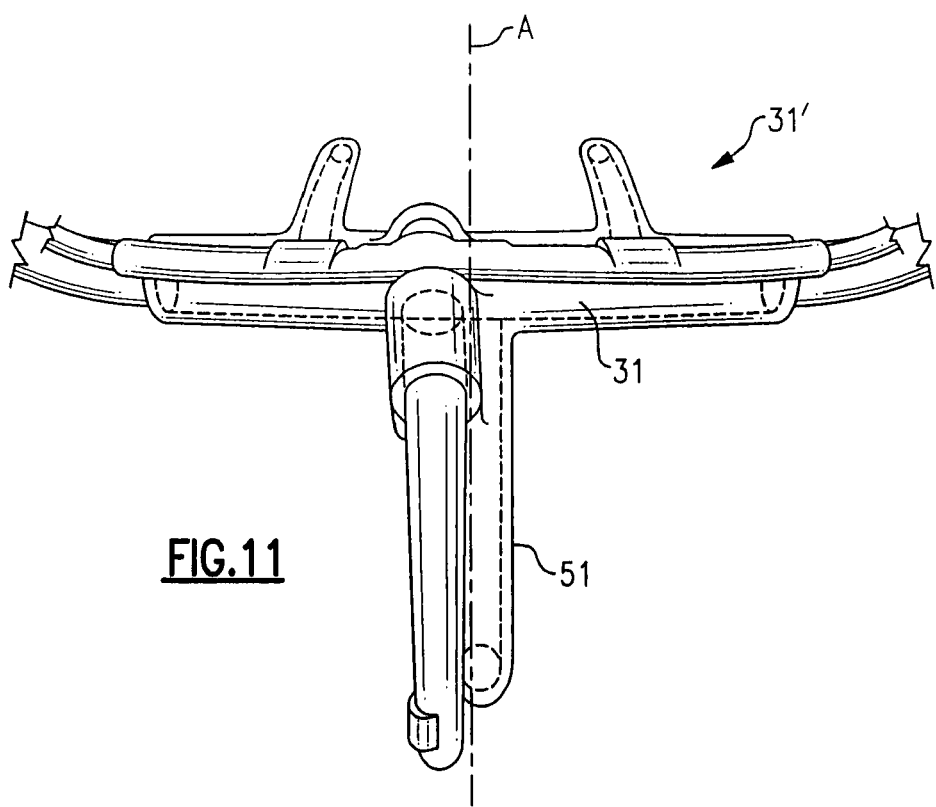
FIG. 11 is a bottom perspective view of the cannula of the second embodiment used to support the temperature sensor.
Figure 12:
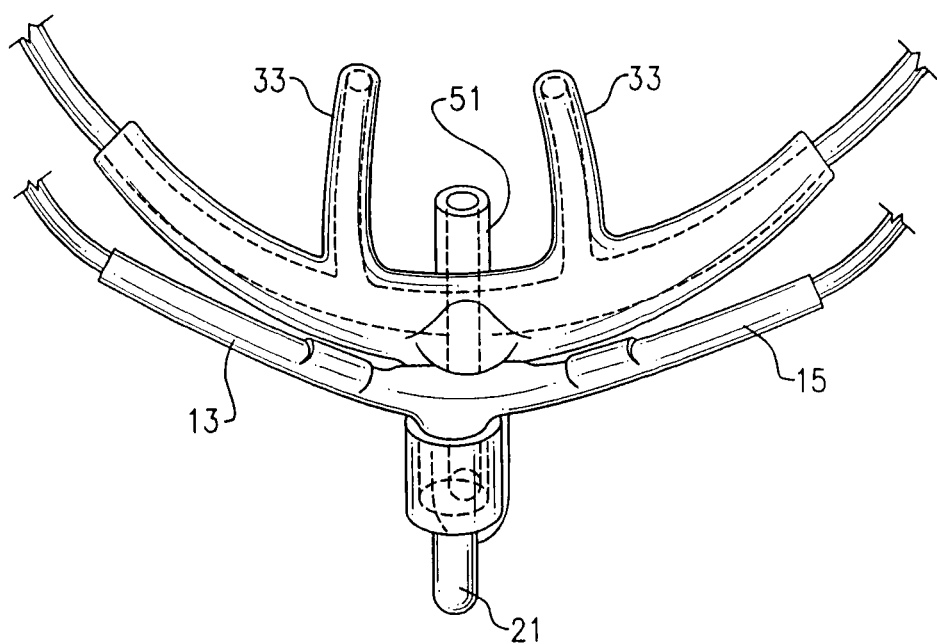
FIG. 12 is a rear view of the cannula of the second embodiment used to support the temperature sensor.

Similar to the description of the first embodiment described with reference to FIGS. 5, 6 and 7, the holster 41 of FIGS. 9, 10 and 11 is provided with the passage 47 and the stop portion 43 to define the receiving notch 45 therebetween into which the center joint of the pressure sensor 1 is located when the temperature sensor 1 is attached with the oral and nasal pressure sensing cannula 31' to create the diagnostic system, as shown and described herein.

For the apparatus and system as described above, the temperature sensor 1 and the pressure sensing cannula 31, 31' can be used together and facilitate obtaining similar but differently processed signals which are indicative of the patient's breathing patterns. The malleability and adjustability of the T-shaped pressure sensor ensures that the left and the right upper branches 13, 15 can be adjusted, in any desired manner, so that they essentially align with the nasal prongs 33 and the nares of the patient's nostrils. The relative flexibility allows the left and the right upper branches 13, 15 as well as the lower branch 21 to be bent inwards or outwards so as to conform to a bend in the cannula body, for instance, as can be seen in FIGS. 5 and 9 while, as can be seen in FIG. 10, the lower branch 21 may be bent so as to achieve an entirely different axial and radial curvature and/or alignment than the oral sensing tube. For example, the free end of the lower branch 21 may be moved in a 360° range of movement, relative to a free end of the pressure sensing tube, and be more accurately placed in the direct airflow of the patient's mouth, relative to the pressure sensing tube, and therefore potentially provide a more accurate data from the patient's respiratory airflow.

With reference now to FIGS. 13A, 13B, 13C, 14 and 15, a detailed description concerning a further embodiment of the present invention will now be provided. As this embodiment is somewhat similar to the previous embodiments, only the differences between this embodiment and the previous embodiments will be discussed in detail.

As with the previous embodiments, the cannula 31" generally comprises a main body 32 which is open at opposed ends thereof (not shown in detail) and has an internal chamber 52 communicating with both open ends of the main body 32. The main body 32 also supports first and second spaced apart nasal prongs 33, 33 which facilitate communication with a respective one of the nostrils of the patient. Each opposed open end of the cannula 31" can be connected, by conventional tubing 54, to suitably detection equipment 56, such as a pressure transducer, for example, and each one of the nares or nasal prongs 33, 33 has an internal passageway 58 which communicates with the internal chamber 52 of the main body 32. According to this embodiment, the internal chamber 52 of the cannula is undivided, that is, the passageway 58 of the first nasal prong 33 communicates with the passageway 58 of the second nasal prong 33 and vice versa, via the internal chamber 52 of the cannula 31". It is to be appreciated that, if desired, the internal chamber 52 of the cannula 31" may be divided, e.g., by a partitioning or dividing wall or septum (not shown), into two completely separate internal chambers such that the dividing wall prevents the passageway 58 of the first nasal prong 33 from communicating, via the internal chamber 52 of the cannula, with the passageway 58 of the second nasal prong 33.

The first and the second nasal prongs 33, 33, as described above, are used to detect breathing of the patient. To facilitate attachment of a desired temperature sensing device, such as a thermistor 60, to the cannula 31" adjacent the first and the second nares or nasal prongs 33, 33, the cannula 31" is provided with a pair of holsters 41 which are spaced apart by a distance of between about 0.125 inches and about 0.5 inches, for example, but aligned with one another, to facilitate receiving and positioning a thermistor at a location precisely between the first and the second nares or nasal prongs 33, 33 of the cannula 31". Each of the aligned holsters 41 have a sensor passage 47 formed therein which extends through the respective holsters 41 to facilitate receiving and supporting the desired temperature sensor 60 therein, such as a thermistor. Each one of the two aligned holsters 41 is typically cylindrical in shape and has a length of between about 0.4 and about 0.5 inches, a through bore of between about 0.08 and about 0.10 inches and a diameter of between about 0.15 and about 0.19 inches. It is to be appreciated that one or both of the holsters 41 may have an elongate cut, slot or opening formed therein (not shown), extending the entire axial length of the side wall of the holster 41, which facilitates the holster(s) 41 expanding somewhat in diameter to allow accommodation of different diameter and/or sized temperature sensors 60, e.g., slightly larger thermistors.

The lead lines 9, 11 and the internal circuitry of the thermistor 60 is typically covered with a plastic overmolded material, or some other protective barrier 28, which protects the internal component of the thermistor 60 and also provides some rigidity to the thermistor 60 to assists with "feeding" or "threading" a leading end of the thermistor 60 through the first and the second aligned sensor passages 47 of the respective first and second holsters 41, 41 so as to be captively retained by the cannula 31". The plastic overmolded material or barrier 28 typically includes a stop feature 62, e.g., an enlarge diameter section or some other stop feature of the plastic overmolded material or barrier 28, that is designed to abut against an end face 64 of the first holster 41 and prevent further or over insertion of the thermistor/plastic overmolded material assembly relative to the first and the second holsters 41, 41.

Following insertion and engagement of the thermistor 60 with the first and second holsters 41, the thermistor 60 is correctly located and positioned between the first and the second nares or nasal prongs 33, 33 of the cannula 31″. As a result of such positioning, the thermistor 60 is precisely located between the first and the second nares or nasal prongs 33, 33 so that the airflow being inspired and expired by the patient will contact the thermistor 60 and facilitate detection of the temperature of the inspired and expired airflow. As with the previous embodiments, the lead lines 9, 11 are coupled to the respiratory airflow detection circuit C for determining the change in temperature across the thermistor 60.

Figure 13C:
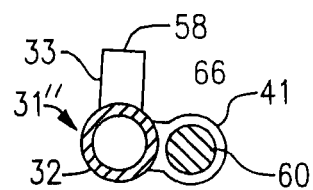
FIG. 13C is a diagrammatic cross-sectional view of the cannula and the temperature sensor of FIG. 13A along section line 13C-13C.
Figure 14:
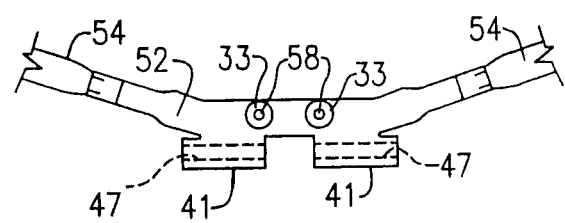
FIG. 14 is a diagrammatic perspective view of the cannula of FIG. 13A prior to be assembled with the temperature sensor.
Figure 15:
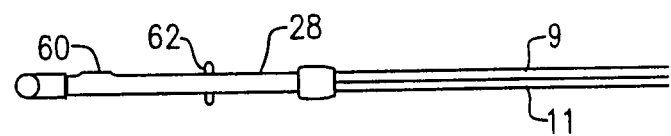
FIG. 15 is a perspective view of the temperature sensor of FIG. 13A with the overmolded material barrier prior to be assembled with the cannula.

An important aspect of this embodiment of the present invention is to sufficiently space the exterior surface 66 of the thermistor 60 from the exterior surface of the main body 32 of the cannula 31″ so as to avoid any contact between those surfaces (see FIG. 13C). It is to be appreciated that if the cannula 31″, or any other surface, is located too close to or contacts the exterior surface 66 of the thermistor 60, this can disrupt accurate temperature sensing by the thermistor 60. Preferably the exterior surface of the thermistor 60 is spaced from the exterior surface of the cannula 31″ by a distance of between about 0.040 and 0.080 inches or so.

It is to be appreciated that although the embodiment shown in FIGS. 13A, 13B, 13C 14 and 15 of the drawings may be utilized with adults, this embodiment is particularly suited for use with smaller patients such as young adults, children and infants.

Since certain changes may be made in the above described improved sleep apnea diagnosing apparatus and method, without departing from the spirit and scope of the invention herein involved, it is intended that all of the subject matter of the above description or shown in the accompanying drawings shall be interpreted merely as examples illustrating the inventive concept herein and shall not be construed as limiting the invention.

Wherefore, we claim:

1. A device for determining a breathing cycle of a patient, the device comprising:
a first sensing device for sensing pressure during the breathing cycle of the patient; and
a second sensing device for sensing temperature of a respiratory airflow of the patient during the breathing cycle concurrently with pressure sensing,
wherein the first sensing device for sensing pressure includes a cannula for receiving a sample of the respiratory airflow from the patient, and the second sensing device comprises at least one thermistor located along a respiratory airflow path of the patient for sensing temperature of the respiratory airflow, and
the cannula includes an integral holster formed from the same material as the cannula so as to be integral with a body of the cannula, the holster extends away from the body of the cannula and comprises a sensor passage by which the holster directly secures the thermistor, relative to the cannula, to facilitate locating the thermistor in a desired region of the respiratory airflow path of the patient,
the holster supports the thermistor such that a portion of the thermistor extends parallel to and along the cannula body so as to be positioned along the respiratory airflow path of the patient in a spaced relationship from both the patient and a first and a second nasal prongs, and
the thermistor is T-shaped and comprises a first nasal branch, a second nasal branch and a lower branch, the lower branch is connected with both the first and second nasal branches, and the lower branch is located between the first and the second nasal prongs and extends through the holster perpendicularly with respect to the body of the cannula, and
the device provides output signals concurrently indicating a measured pressure and a measured temperature of the breathing cycle.

2. The device according to claim 1, wherein the exterior surface of the thermistor is spaced from the exterior surface of body of the cannula by a distance of between about 0.040 and 0.080 inches so as to avoid contact between those surfaces.

3. The device according to claim 1, wherein the thermistor is coupled to a temperature sensing circuit which includes a test circuit which comprises a switch, a first light emitting diode and a second light emitting diode: the switch comprises a first state in which the switch is open and a second state in which the switch is closed to facilitate indicating continuity of the temperature sensing circuit for the thermistor, and the first light emitting diode indicates an integrity of a first lead of the test circuit while the second light emitting diode indicates an integrity of a second lead of the test circuit.

4. The device according to claim 1, wherein the first and the second nasal prongs each communicate, during use, with one nostril of the patient.

5. The device according to claim 1, wherein the first and the second nasal prongs each communicate, during use, with one nostril of the patient and the cannula further includes an oral prong which has an oral flow passage which communicates with an oral respiratory airflow path of the patient, and the oral prong is positioned along a central plane spaced equidistant between the first and the second nasal prongs.

6. The device according to claim 5, wherein a free end of the lower branch of the thermistor has an exterior surface which is contoured so that the free end of the lower branch tends to be ejected and forced away from one of teeth and gums of a young child or infant in the event that the young child or infant attempts to one of suck, bite, and chew on the free end of the lower branch of the thermistor.

7. The device according to claim 5, wherein a free end of the lower branch of the thermistor has an end cap which is contoured so that the free end of the lower branch tends to be ejected and forced away from one of teeth and gums of an individual.

8. The device according to claim 1, wherein the thermistor is covered with an overmolded material which protects and provides rigidity to the thermistor to assist with feeding a leading end of the thermistor through the sensor passage of the holster so that the thermistor can be captively retained by the holster of the cannula; and
the cannula includes a stop feature which abuts against an end face of the holster and prevents further insertion of the thermistor.

9. The device according to claim 1, wherein an exterior surface of the thermistor is located adjacent to but sufficiently space from an exterior surface of the cannula so as to avoid contact therewith.

10. A device for determining a breathing cycle of a patient, the device comprising:
a cannula forming a first sensing device for sensing pressure during the breathing cycle of the patient; and
a second sensing device for sensing temperature of respiratory airflow during the breathing cycle of the patient concurrently with the pressure sensing;
wherein the cannula further comprises a left branch, a right branch, a lower branch, and at least an integral holster formed from the same material as the cannula so as to be integral with a body of the cannula, the holster extends away from the body of the cannula and comprises a sensor passage by which the holster solely secures the second sensing device, relative to the cannula, and located the second sensing device along a path of the respiratory airflow of the patient so that the second sensing device provides an output signal indicating the concurrently measured pressure and temperature during the breathing cycle of the patient, and the holster supports a thermistor such that the thermistor extends parallel to and along the body of the cannula and is spaced from both the patient and a first and second nasal prongs of the cannula;

the second sensing device is at least partially covered with an overmolded material which provides the second sensing device with rigidity;

the second sensing device is solely support by the cannula via engagement between the at least integral holster and the second sensing device;

the first sensing device for sensing pressure comprises the first and second nasal prongs which each communicate, during use, with a respective nostril of the patient and an oral prong with an oral flow passage that communicates with an oral respiratory airflow path of the patient, and the oral prong is positioned along a central plane spaced equidistant between the first and the second nasal prongs and the second sensing device comprises the thermistor, located in the path of the respiratory airflow path, for sensing temperature of the respiratory airflow;

the thermistor is T-shaped and comprises a first nasal branch, a second nasal branch and a lower branch, the lower branch is connected with both the first and second nasal branches, and the lower branch is located between the first and the second nasal prongs and extends through the holster perpendicularly with respect to the body of the cannula, a temperature sensing circuit, coupled to the thermistor, includes a test circuit which comprises a switch having a first state, in which the switch is open, and a second state, in which the switch is closed, to facilitate for indicating continuity of the temperature sensing circuit for the thermistor; and the at least integral holster has a length of between about 0.4 and about 0.5 inches, a sensor passage diameter of between about 0.08 and about 0.10 inches and an outer diameter of between about 0.15 and about 0.19 inches.

11. A device for determining a breathing cycle of a patient, the device comprising:

a first sensing device for sensing pressure during the breathing cycle of the patient, and a second sensing device for sensing temperature of a respiratory airflow of the patient during the breathing cycle concurrently with pressure sensing, wherein the first sensing device for sensing pressure includes a cannula for receiving a sample of the respiratory airflow from the patient, and the second sensing device comprises at least one thermistor located along a respiratory airflow path of the patient for sensing temperature of the respiratory airflow, the thermistor is T-shaped and comprises a first nasal branch, a second nasal branch and a lower branch, the lower branch is connected with both the first and second nasal branches, and the lower branch is located between the first and the second nasal prongs and extends through the holster perpendicularly with respect to the body of the cannula, the cannula includes an integral holster formed from the same material as the cannula so as to be integral with a body of the cannula, the holster extends away from the body of the cannula and comprises a sensor passage by which the holster directly secures the thermistor, relative to the cannula, to facilitate locating the thermistor in a desired region of the respiratory airflow path of the patient, the holster supports the lower branch of the thermistor such that the first and the second nasal branches of the thermistor extend parallel to and along the cannula body so as to be positioned along the respiratory airflow path of the patient in a spaced relationship from both the patient and the first and the second nasal prongs, and the device provides output signals concurrently indicating a measured pressure and a measured temperature of the breathing cycle.

12. The device according to claim 11, wherein the cannula further includes an oral prong which has an oral flow passage which communicates with an oral respiratory airflow path of the patient, and the oral prong is positioned along a central plane spaced equidistant between the first and the second nasal prongs.

* * * * *